United States Patent [19]

Takeuchi

[11] Patent Number: 5,072,734
[45] Date of Patent: Dec. 17, 1991

[54] PULSE DOPPLER MTI SYSTEM

[75] Inventor: Yasuhito Takeuchi, Tokyo, Japan

[73] Assignee: Yokogawa Medical Systems, Limited, Tokyo, Japan

[21] Appl. No.: 457,775

[22] PCT Filed: Jul. 14, 1988

[86] PCT No.: PCT/JP88/00697

§ 371 Date: Jan. 11, 1990

§ 102(e) Date: Jan. 11, 1990

[87] PCT Pub. No.: WO89/00402

PCT Pub. Date: Jan. 26, 1989

[30] Foreign Application Priority Data

Jul. 14, 1987 [JP] Japan .................. 62-175629

[51] Int. Cl.$^5$ .............................................. A61B 8/00
[52] U.S. Cl. ........................ 128/660.05; 128/661.09; 128/660.07
[58] Field of Search ............. 128/660.05, 661.09, 128/661.07, 661.08, 660.07

[56] References Cited

U.S. PATENT DOCUMENTS

| | | | |
|---|---|---|---|
| 4,417,584 | 11/1983 | Cathignol et al. | 128/661.08 |
| 4,768,515 | 9/1988 | Namekawa | 128/661.09 |
| 4,790,321 | 12/1988 | Miwa et al. | 128/660.07 |
| 4,809,249 | 2/1989 | Barnes | 128/661.08 |
| 4,817,614 | 4/1989 | Hassler et al. | 128/660.05 |
| 4,896,674 | 1/1990 | Seo | 128/661.09 |
| 4,918,605 | 4/1990 | Shirasaka | 128/660.05 |
| 4,966,151 | 10/1990 | Takeuchi | 128/660.05 |

Primary Examiner—Francis Jaworski
Assistant Examiner—George Manuel
Attorney, Agent, or Firm—Moonray Kojima

[57] ABSTRACT

A pulse Doppler MTI system for equally displaying movements in any directions within a tomographic plane is characterized by creating a bipolar video signal file in which receive signals for one scan serve as one frame and performing a two-dimensional cross-correlation process on the file data after removing components associated with fixed reflecting points.

2 Claims, 3 Drawing Sheets

BOXEL (SAMPLE AREA) 32

PULSE DOPPLER MTI SYSTEM

DESCRIPTION

1. Technical Filed

The present invention is directed to a pulse Doppler MTI system for equally displaying movement in any directions within a tomographic plane.

2. Background Arts

When a subject for examination undergoes radiation of ultrasound pulses, echoes return from the reflection body. If the reflection body is moving, a frequency of the echoes to be received differs from a transmitting frequency. When the reflection body moves towards a probe, a receiving frequency is higher than the transmitting frequency. Whereas in the case of moving away from the probe, the receiving frequency drops down. A deviation in frequency is proportional to a kinetic velocity of the reflection body. It is possible to detect both a direction in which the blood flows within, e.g., a heart or blood vessels and a flowing speed by utilizing the Doppler effect. The ultrasound pulses are reflected typically from a solid body and from a moving body. Where the attention is paid particularly on the moving body, only reflection signals from the moving body are displayed, while the reflection signals from the solid body are erased. This arrangement facilitates a recognition thereof. For this purpose, there is employed a moving target indicator (hereinafter abbreviated to MTI) system for fetching only the reflection signals coming from the moving body. This type of MTI system has hitherto involved use of an MTI filter, wherein one irradiation ultrasound beam (hereinafter referred to as a sound ray) is dealt with in regards to data on RF signals or equiphase signals (hereinafter referred to as i-signals) of a bipolar video which are obtained by effecting a coherent detection and orthogonal signals (hereinafter referred to as q-signals); and there are grasped variations in time between phasic distributions in an irradiating direction of the ultrasound waves, i.e., in a radial direction. In the case of adopting a multi-beam receiving system, the above-mentioned signal process is merely performed on the respective beams. In an ultrasound diagnosing device for circulatory organs, when measuring a velocity of a blood flow, the direction thereof is limited to the radiant direction, and velocity components can not absolutely be measured with respect to the components right-angled to the sound rays. Hence, it is impossible to accurately measure the flowing velocity. Especially in connection with the blood vessels orthogonal to the sound rays, the flowing velocity and kinetic direction of the blood can not be measured. The accurate measurement of the blood flow requires performing a two-dimensional MTI process in which the components orthogonal to the radiant direction are added as well as processing in the radiant direction.

A video MTI (incoherent MTI) is capable of equally detecting the movements in any directions within a tomographic plane, and hence probably this method can sufficiently be applied. In the MTI after effecting a video detection, however, it is feasible to observe an image of an ambiguous flow in the middle of, e.g., a portal vein. Echoes of the blood flow, or rather the echoes of the blood itself appear as speckle noises, so that there is less chance to obtain a well-shaped image even by indicating an amplitude thereof. Therefore, it is desirable to image-display the signals having a higher fidelity to the development in the form of complex quantities as they are without effecting no video detection.

DISCLOSURE OF THE INVENTION

It is a primary object of the present invention to actualize a pulse Doppler MTI system for equally displaying movements in any directions within a tomographic plane.

The present invention is characterized by the steps of creating a file of bipolar video signals in which receiving signals for one scan serve as one frame on the basis of echo receiving signals of a plurality of scanning processes associated with receive multi-beam forming, and effecting a two-dimensional cross-correlation process after eliminating components relative to fixed reflecting points with respect to data on this file.

BEST MODE FOR CARRYING OUT THE INVENTION

Figure 1:
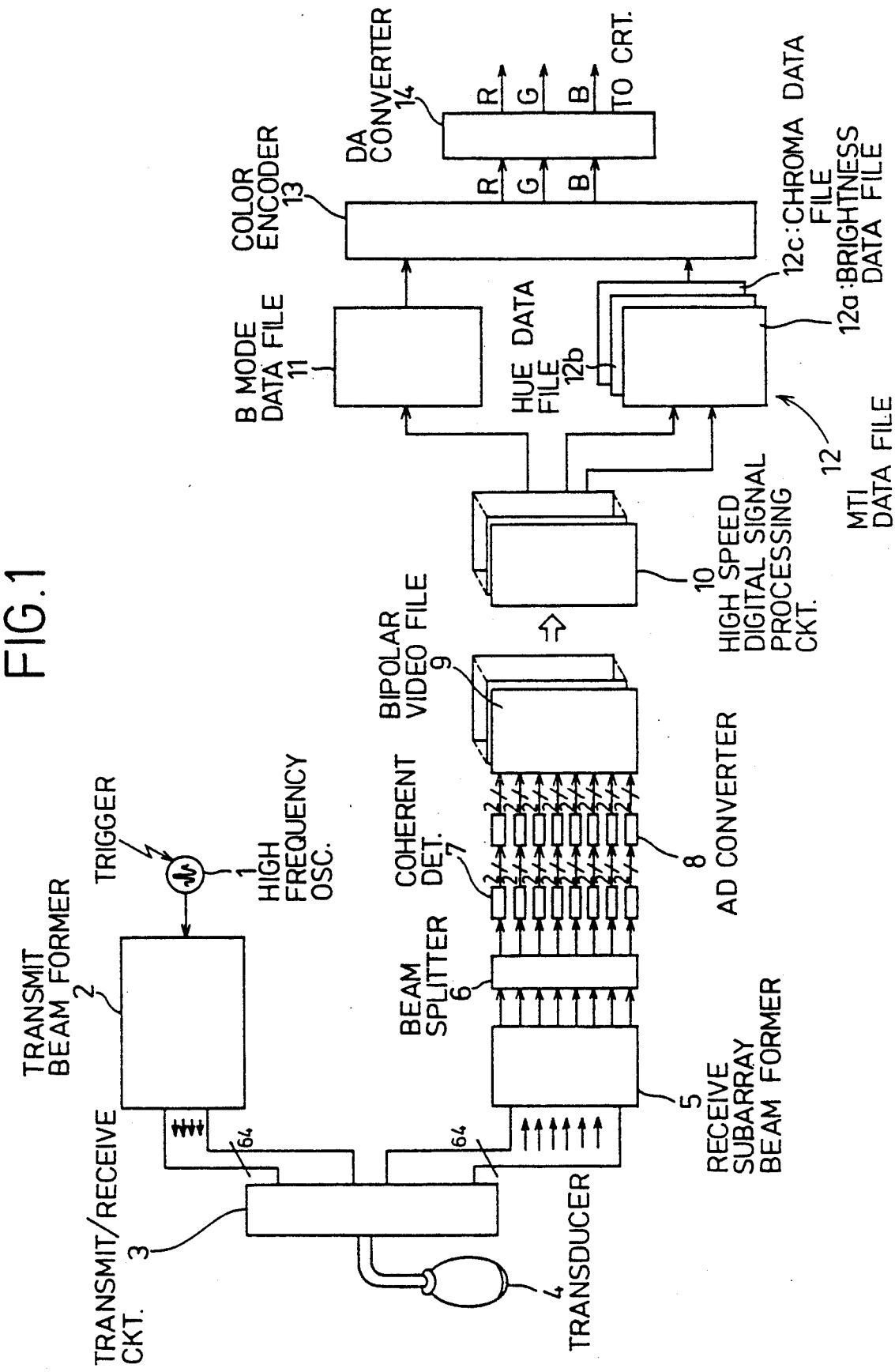
FIG. 1 is a schematic diagram illustrating one embodiment of the present invention.
Figure 2:
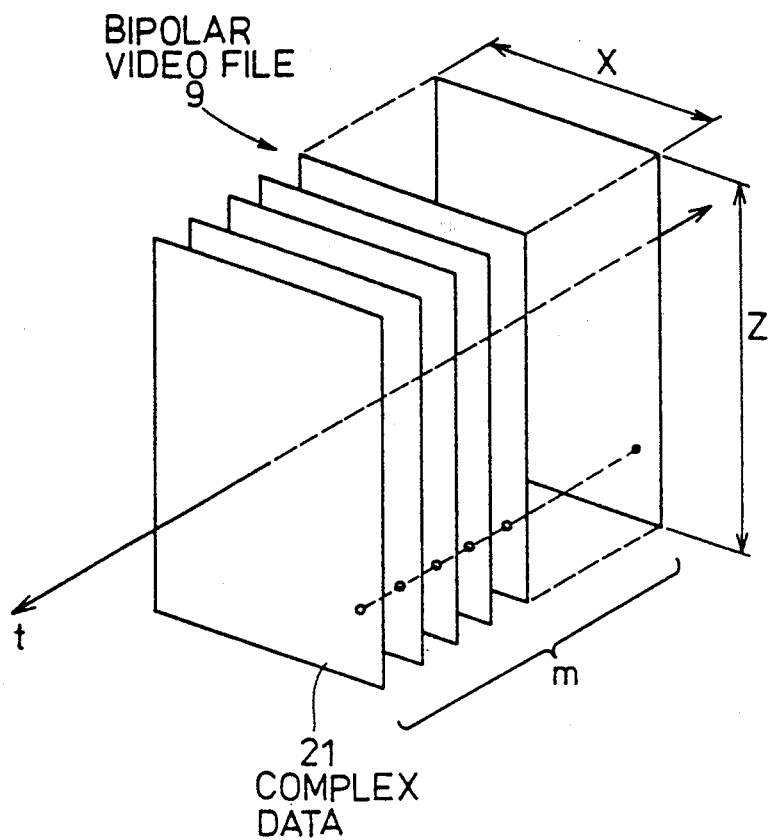
FIG. 2 is a diagram depicting a structure of a bipolar video file.

Turning first to FIG. 1, there is a schematic diagram of one embodiment of the present invention. Designated at in FIG. 1 is a high frequency oscillator for generating high frequency signals intended to transmit ultrasound waves upon receiving transmit triggers, output signals of which undergo a delay process enough to transmit fan beams in a transmit beam former 2, thereby outputting signals of 64 channels. The numeral 3 represents a transmit/receive circuit; and 4 an ultrasound probe including 64 pieces of vibrator elements for transmitting, into a subject for examination, ultrasound signals into which transmit high frequency signals from the transmit/receive circuit 3 are converted, and then effecting a conversion into high frequency receive signals by receiving reflection waves from the subject. 64-channel high frequency receiving signals of the outputs of the ultrasound probe are inputted via the transmit/-receive circuit 3 to a receive subarray beam former 5. The receive subarray former 5 arranges multi-beam receiving 64-channel inputs having different delays to exhibit a ratio of 8:1 and outputs them. Indicated at 6 is a beam splitter having a function to change the signals arranged at the ratio of 8:1 in the receive subarray beam former 5 into outputs of 8 beams having slightly different angles, outputs of which are detected by a coherent detector 7 and then converted into digital signals by means of an AD converter 8. The thus converted digital signals are written to a bipolar video file 9. Referring to FIG. 2, there is illustrated a structure of the bipolar video file 9, wherein the file 9 is constructed of m-pieces of frames each used for data of one scan. Each frame is arranged such that the axis of abscissa (Z-axis) is a depthwise direction of the sound rays, while the axis of ordinate (X-axis) is a direction in which n-streaks of sound rays are arrayed; and complex data on the i-signals and the q-signals are written to each address. The data with respect to n-streaks of sound rays on the X-axis can simultaneously be obtained by receiving the multi-beams. Hence, the complex data 21 penetrating m-pieces of frames are conceived as data per scan by the waves reflected from the same position. Referring back to FIG. 1, the numeral 10 denotes a high-speed digital signal processing circuit for simultaneously executing both an MTI process and a B-mode display process relative to the data stored in the bipolar video file 9, and actualization of the circuit 10 involves the use of a high-speed processor or the like. In the outputs of the high-speed digital signal processing circuit 10, the data which have undergone the B-mode display process are written in a standard TV format to a B-mode data file 11. The MTI-processed data are written in the standard TV format to an MTI data file 12 consisting of a brightness data file 12a, a hue data file 12b and a chroma data file 12c. Designated at 13 is a color encoder for reading the black-and-white brightness data from the B-mode data file 11, separating them into 3 primary color data of R, G and B, and classifying the brightness, hue and chroma data read from the MTI data file 12 into the 3 primary color data of R, G and B. RGB output signals are converted into analog signals by a DA converter 14 and then displayed on a CRT (not illustrated).

The description will next be focused on the operation of the thus constructed embodiment. High frequency signals outputted from the high frequency oscillator 1 are converted into 64-channel signals which serve to form fan beams in the transmit beam former 2 and inputted via the transmit/receive circuit 3 to the ultrasound probe 4. The 64-channel high frequency signals supplied to 64 pieces of vibrator elements of the ultrasound probe 4 are converted into ultrasound waves to form the fan beams with which an interior of the subject for examination is irradiated. The ultrasound waves reflected from the subject are received by the ultrasound probe 4 and then converted into high frequency signals having amplitudes and phases that differ depending on conditions of the reflection body. The high frequency signals passing through the transmit/receive circuit 3 are inputted to the receive subarry beam former 5, thereby outputting 8-channel signals as data associated with a plurality of sound rays. The 8-channel signals are phased to vibrate the beams little by little, wherein the signals arranged to exhibit the ratio of 8:1 in the receive subarray beam former 5 serve as outputs of 8 beams having angles slightly different from each other. The phased output signals are detected by the coherent detector 7 and separated into the i-signals and the q-signals. The thus separated signals are converted into digital signals by means of the AD converter 8. The digitized complex signals are stored into the bipolar video file 9, in which place, as stated earlier, the data are stored in the B-mode display format into each frame with a configuration depicted in FIG. 2. Since a single frame is constructed per scan, a line drawn to penetrate m-pieces of frames is defined as a time axis t. In the Figure, the file is composed of m-pieces of frames each storing the complex data on n-streaks of sound rays, which implies that it has $(2 \times m \times n)$ pieces of depthwise data filees.

Figure 3A:
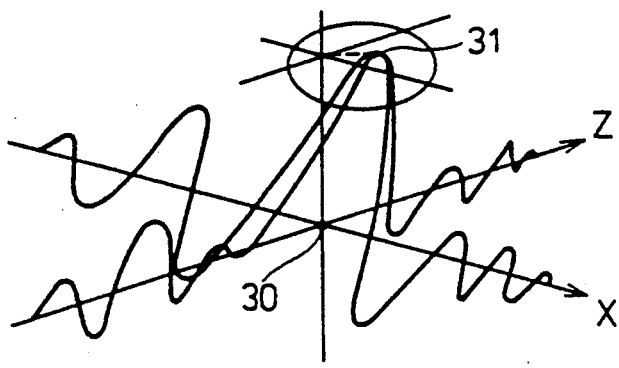
FIGS. 3A and 3B are diagrams of assistance in explaining a two-dimensional cross-correlation process.
Figure 3B:
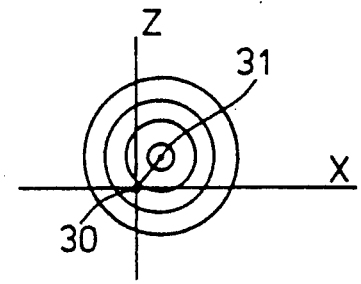

Preparatory to the MTI display, the high-speed digital signal processing circuit 10 reads out the signals of the bipolar video file 9 and effects the following arithmetic operation. The arithmetic operation starts with execution of high-pass processes in a t-axial direction of FIG. 2 with respect to all the file data to eliminate fixed target data from the file data, thus removing DC components based on the fixed target. At this time, the output signals generated as a result of processing are obtained singly for each of a series of k-frames on condition that k is the processing degree. There is given forth no output for the inputs from the first signal to the $(k-1)$th signal. After inputting the k-th signal, the signals are singly outputted each time. Based on these outputs, the frames of the MTI data are sequentially created. Subsequently, the two-dimensional cross-correlation is computed between the MTI data frames adjacent to each other. As a result of the two-dimensional cross-correlation, a peak is present in a position deviating from an origin. A movement of the reflection body can be recognized from a direction and an amount of deviation. This aspect is shown in FIGS. 3A and 3B. FIG. 3A is a schematic diagram of assistance in explaining the two-dimensional cross-correlation. FIG. 3B is a diagram of the situation of FIG. 3A as taken from above, depicting a deviation from the origin. In these FIGURES, the numeral 30 stands for an origin at which the X-axis intersects the Z-axis; and 31 a peak point generated by effecting the two-dimensional cross-correlation process on X-axis component data and Z-axis component data of the MTI data. FIGS. 3A and 3B show a state where the peak point 31 deviates from the origin 30 and also a movement of the reflection body within the frame plane depicted in FIG. 2.

The foregoing method will be described by way of one example. Supposing that a bipolar video file 9 illustrated in FIG. 2 is given in connection with, e.g., 16-frame continuous transmitting/receiving operations, in this case m=16, and hence 9 pieces of MTI frames are obtained when performing the MTI process by combining 8 sets of adjacent frames among them. Signals of the frames contiguous to each other are processed in accordance with the two-dimensional cross-correlation, thereby acquiring 8 pieces of cross-correlation images from the 9 MTI frames. These cross-correlation images may be divided simply by 8 to obtain a mean value for improving an SN ratio; or alternatively a weighted mean value may be obtained by weighting in the vicinity of the center thereof. In addition, the values held are replaced some percentage invariably with new input data—i.e., a so-called moving average may be affected. The frames of the cross-correlation images can thus be obtained on the basis of the data in which data on the 8 frames are averaged.

Figure 4:
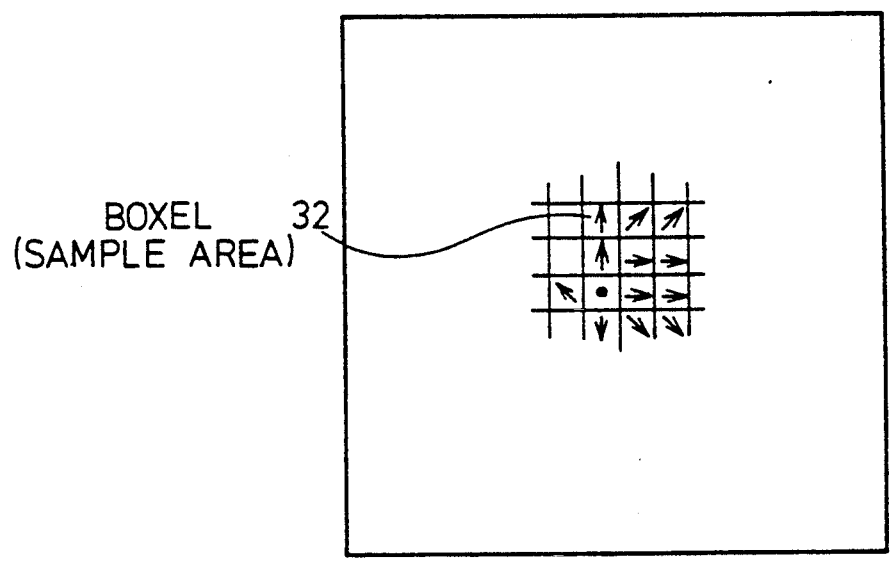
FIG. 4 is a diagram illustrating a vector of flow per sample area on a frame of the bipolar video file.

As a matter of fact, the above-mentioned process is carried out per section of a sample area in which the respective frames of the video data file are minutely sectioned. This process is repeated corresponding to the number of the sample areas, which implies that the whole two-dimensional plane is processed. A size of the sample area is set substantially equal to, e.g., several wavelengths, or 16 to 32 points in RF in the form of sampling points, or 8 to 16 streaks in parallel frequency of the multi-beams. The requirement is satisfied, if approximately $(64 \times 64)$ pieces of sample areas are provided on the entire two-dimensional plane. Based on this sample area unit, a flow vector is, as illustrated in FIG. 4, recognized for every sample area. Referring again to FIG. 4, the numeral 32 designates one sample area. The foregoing process is executed by the high-speed digital signal processing circuit 10, thereby obtaining the X-axial movements within the frame plane, viz., the MTI data in all directions, including the movement in the tangent direction.

Figure 5:
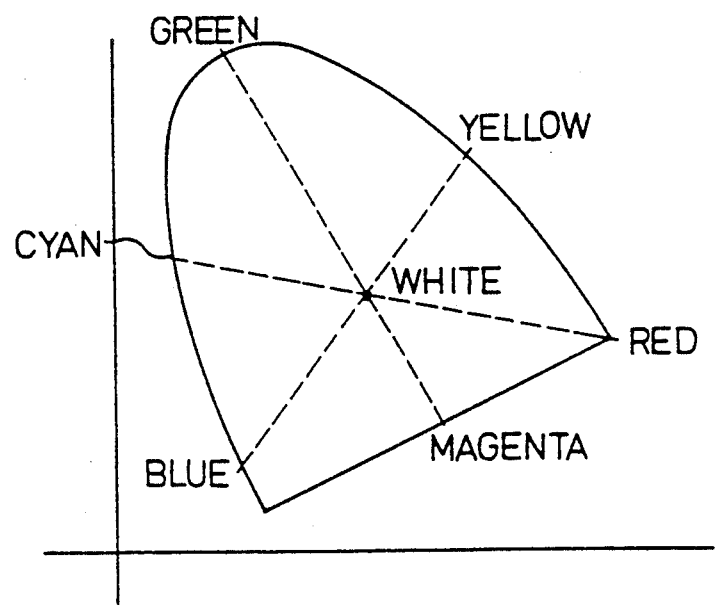
FIG. 5 is a graphic chart showing chromaticities.

The MTI data are inputted in the TV format to the MTI data file 12, while the data for the B-mode display on the bipolar video file are inputted in the TV format to the B-mode data file 11. In order to color-display the MTI data, the brightness data are stored in a brightness data file 12a; the hue data in a hue data file 12b; and the chroma data in a chroma data file 12c. A displaying method is, it can be considered, arranged in such a way that two axes are, unlike a prior art color Doppler, required because of displaying the vectors, and preferably complementary colors are employed for those which differ by 180° in direction. Turning now to a chromaticity table of FIG. 5, the Doppler shift in the same Z-direction as that in the prior art, i.e., in the normal direction is expressed by use of a red-cyan or magenta-green axis, and the shift in the X-axial direction, viz., in the tangent direction is expressed by use of an orange-purple or yellow-blue axis. The red-cyan axis used herein implies that, for instance, an approaching direction is expressed in red, whereas a go-away direction is expressed in cyan. Moving away from a neutral color like a white or gray indicates a large deviation of the correlation peak from the origin. The neutral color implies that there is no shift. Note that there may be added a method of expressing a degree of the correlation peak in color brightness. Allocations are made in this manner. Read out in the TV format are the data stored in the MTI data file 12 and the B-mode display brightness data stored in the B-mode data file 11 which are in turn converted into three primary color data of R, G and B by means of a color encoder 13. The three primary color data are converted further into analog signals by a DA converter 14 for displaying them on a CRT. With this arrangement, it is possible to grasp not only the movement in the normal direction conceived as the conventional visual line direction but also the movement in the tangent direction orthogonal thereto and further color-display them.

It is to be noted that the present invention is not limited to the embodiment discussed above. For example, the step of increasing the SN ratio by inter-frame averaging in the two-dimensional cross-correlation process stated in the embodiment may be omitted in the case of a flow a high velocity in, e.g., the heart or large blood vessels with a good SN ratio, thereby attaining a speed-up. Moreover, instead of averaging the two-dimensional images formed by correlation values between the frames, averaging may be carried out by adding those obtained by effecting an absolute value comparison (square mean value) or squaring the data which have been separated into the orthogonal components. This leads to a reduction in fluctuation attributed to the speckles. Besides, the color allocations performed as a coloring method may arbitrarily be selected, and a degree of the correlation peak may also be expressed in color brightness.

Although the best mode for carrying out the present invention has been described, a variety of modifications can be performed with facility by one having ordinary knowledge about the technical field to which the present invention belongs without departing from the scope of the claims which follow.

What is claimed is:

1. In a pulse Doppler MTI system capable of simultaneously performing a B-mode display and an MTI display using format based on multi-beam scanning, the improvement comprising video storage means comprising a plurality of frames, for storing bipolar video data, obtained by coherent detection, in one of said plurality of frames for each scan;

means for eliminating fixed target components from data entered in said plurality of frames;

processing means for two-dimensional cross-correlating data stored in adjacent frames;

arithmetic means for obtaining a kinetic vector within a frame plane from output signals from said processing means; and coloring means for displaying orthogonal components of said kinetic vector within said frame plane.

2. The system of claim 1, wherein said coloring means use a chromaticity table comprising a complementary axis of red-cyan or magenta-green representing movement on a normal axis, and a complementary color axis of orange-purple or yellow-blue representing movement on a tangent axis.

* * * * *